025B2

US009221790B2

(12) United States Patent
Kim et al.

(10) Patent No.: US 9,221,790 B2
(45) Date of Patent: Dec. 29, 2015

(54) BENZAMIDE DERIVATIVES

(75) Inventors: Soon-Hoe Kim, Gyeonggi-do (KR);
Weon-Bin Im, Gyeonggi-do (KR);
Sung-Hak Choi, Gyeonggi-do (KR);
Sun-Ho Choi, Seoul (KR); Ju-Hee Sohn, Seoul (KR); Hyun-Jung Sung, Gyeonggi-do (KR); Mi-Yeon Kim, Gyeonggi-do (KR); Kang-Hun Cho, Gyeonggi-do (KR); Tae-Kyoung Sohn, Gyeonggi-do (KR)

(73) Assignee: Dong-A Pharm. Co., Ltd., Seoul (KR)

( * ) Notice: Subject to any disclaimer, the term of this patent is extended or adjusted under 35 U.S.C. 154(b) by 242 days.

(21) Appl. No.: 13/641,867

(22) PCT Filed: Apr. 18, 2011

(86) PCT No.: PCT/KR2011/002759
§ 371 (c)(1),
(2), (4) Date: Nov. 21, 2012

(87) PCT Pub. No.: WO2011/132901
PCT Pub. Date: Oct. 27, 2011

(65) Prior Publication Data
US 2013/0085160 A1 Apr. 4, 2013

(30) Foreign Application Priority Data
Apr. 23, 2010 (KR) .................. 10-2010-0038039

(51) Int. Cl.
*C07D 211/26* (2006.01)
*C07D 401/06* (2006.01)

(52) U.S. Cl.
CPC .......... *C07D 401/06* (2013.01); *C07D 211/26* (2013.01)

(58) Field of Classification Search
None
See application file for complete search history.

(56) References Cited

U.S. PATENT DOCUMENTS

| | | | |
|---|---|---|---|
| 4,138,492 A | 2/1979 | Noverola et al. | 424/267 |
| 4,962,115 A | 10/1990 | Van Daele | 514/326 |
| 5,057,525 A | 10/1991 | Van Daele | 514/318 |
| 5,137,896 A | 8/1992 | Van Daele | 514/327 |
| 5,864,039 A | 1/1999 | Kawakita et al. | 546/229 |
| 8,030,315 B2 | 10/2011 | Kim et al. | 514/255.01 |
| 2010/0093801 A1 | 4/2010 | Chung et al. | 514/331 |
| 2010/0105727 A1 | 4/2010 | Yoo et al. | 548/400 |
| 2013/0072459 A1 | 3/2013 | An et al. | 514/81 |
| 2013/0281492 A1 | 10/2013 | Rhee et al. | 514/340 |
| 2013/0296571 A1 | 11/2013 | Son et al. | 546/75 |
| 2013/0317052 A1 | 11/2013 | Son et al. | 514/289 |
| 2014/0017345 A1 | 1/2014 | Kim et al. | 424/725 |
| 2014/0044817 A1 | 2/2014 | Kim et al. | 424/773 |
| 2014/0155609 A9 | 6/2014 | Son et al. | 546/75 |

FOREIGN PATENT DOCUMENTS

| | | |
|---|---|---|
| CN | 101641330 A | 2/2010 |
| EP | 0774460 | 5/1997 |
| KR | 10-1997-0702247 | 5/1997 |
| WO | WO 99/02494 | 1/1999 |
| WO | WO 00/31033 | 6/2000 |
| WO | WO 2008/114971 | 9/2008 |
| WO | WO 2010/062959 | 6/2010 |

OTHER PUBLICATIONS

Itoh, K et al Eur J Med Chem 1999 vol. 34 p. 977-989.*
Gilchrist, T. "Heterocyclic Chemistry" London, Addison Wesley Longmans 1997, pp. 26-29.*
Claeysen, S. et al., Mol. Pharmacol. 2000 vol. 58 pp. 977-989.*
Silverman, R. "The Organic Chemistry of Drug Design and Drug Action," 2004, Elsevier, pp. 29-32.*
Letter/Written Disclosure of the Supplemental Information Disclosure Statement for the above-referenced application, submitted on Nov. 7, 2014, 2 pages.
Bylov et al., "Synthesis and anti-inflammatory activity of N-substituted 2-oxo-2H-1-benzopyran-3-carboxamides and their 2-iminoanalogues," Eur. J. Med. Chem. 34:997-1001 (1999).
Examination Report, issued Jul. 29, 2013, in connection with Australian Patent Application No. 2011243393, 3 pages.
Response to Examination Report, submitted Feb. 27, 2014, in connection with European Patent Application No. 11772189.4, 26 pages.
Response to Examination Report, submitted Jun. 11, 2014, in connection with Australian Patent Application No. 2011243393, 36 pages.
Notice of Allowance, issued Jul. 8, 2014, in connection with Australian Patent Application No. 2011243393, 12 pages.
Examination Report, issued Jul. 21, 2014, in connection with New Zealand Patent Application No. 602612, 2 pages.
Letter/Written Disclosure of the Information Disclosure Statement for the above-referenced application, mailed on Oct. 25, 2013, 2 pages.
Claeysen et al., "Pharmacological properties of 5-Hydroxytryptamine4 receptor antagonists on constitutively active wild-type and mutated receptors," Molecular Pharmacology 58(1):136-144 (2000).
Dong-A Group website, "R&D at Dong-A," copyright 2009 [online][retrieved on Jul. 7, 2013] Retrieved from:<URL:en.donga.co.kr/rnd/rnd01.jsp, 1 page.

(Continued)

*Primary Examiner* — Heidi Reese
(74) *Attorney, Agent, or Firm* — Dentons US LLP; Stephanie Seidman; Frank J. Miskiel

(57) ABSTRACT

The present invention provides a novel benzamide derivative or a pharmaceutically acceptable salt thereof, a method for preparing the same, and a 5-$HT_4$ receptor agonist containing the same as an active ingredient. Benzamide derivatives of the present invention have a superior affinity for 5-$HT_4$ receptors, a capability to reduce a gastric emptying time and a low toxicity, and consequently are therapeutically effective for the treatment of a variety of diseases associated with 5-$HT_4$ receptors.

21 Claims, No Drawings

(56) References Cited

OTHER PUBLICATIONS

Dong-A Group website, "Research Center," copyright 2009 [online][retrieved on Jul. 7, 2013] Retrieved from:<URL:en.donga.co.kr/rnd/rnd02, 2 pages.

Dong-A Group website, "Pipeline," copyright 2009 [online][retrieved on Jul. 7, 2013] Retrieved from:<URL:en.donga.co.kr/rnd/rnd03.jsp, 2 pages.

Wyngaert et al., "Cloning and expression of a human serotonin 5-HT4 receptor cDNA," J Neurochem. 69(5):1810-1819 (1997).

Office Action, issued Jul. 3, 2013, and translation, in connection with Chinese Patent Application No. 201180020476.6, 14 pages.

Extended European Search Report, issued Aug. 8, 2013, in connection with European Patent Application No. 11772189.4, 4 pages.

Letter/Written Disclosure of the Information Disclosure Statement for the above-referenced application, mailed on Jan. 15, 2013, 2 pages.

Bockaert et al., "5-HT 4 Receptors," CNS Drugs, 1:6-15 (1994).

Bockaert et al., "The 5-HT 4 Receptor: a place in the sun," Trends in Pharmacol. Sci., 13:141-145 (1992).

Eglen et al., "Central 5-HT 4 Receptors," Trends in Pharmacol. Sci., 16:391-398 (1995).

English Abstract of WO 1995/026953 (Corresponding International Application of KR-10-1997-0702247), 2 pages.

Ford et al., "The 5-HT 4 Receptor," Med. Res. Rev., 13:633-662 (1993).

Gullikson et al., "Gastrointestinal Motility Responses to the S and R Enantiomers of Zacopride, a 5-HT4 Agonist and 5-HT3 Antagonist," Drug Dev. Res., 26:405-417 (1992).

Itoh et al., "Synthesis and pharmacological evaluation of carboxamide derivatives as selective serotoninergic 5-HT 4 receptor agonists," Eur. J. Med. Chem. 34:329-341 (1999).

Iwanaga et al., "Stimulatory Effect of N-[4-[2-(Dimethylamino)ethoxy]benzyl]-3,4-Dimethoxybenzamide Hydrochloride (HSR-803) on Normal and Delayed Gastrointestinal Propulsion," Jpn J Pharmacol. 56(3):261-269(1991).

Kaumann et al., "A 5-HT 4-like receptor in human right atrium," Naunyn-Schmiedeberg's Arch Pharmacol 344:150-159 (1991).

Romanelli et al., "Synthesis and Biological Activity of a Series of Aryl Tropanyl Esters and Amides Chemically Related to 1H-Indole-3-carboxylic Acid endo 8-Methyl-8-azabicyclo[3,2,1]oct-3-yl Ester," Arzheim Forsch./Drug Res. 43: 913-918 (1993).

Sonda et al., "Design and synthesis of orally active benzamide derivatives as potent serotonin 4 receptor agonist," Bioorganic & Medicinal Chemistry 11:4225-4234 (2003).

Sonda et al., "Synthesis and pharmacological evaluation of benzamide derivatives as selective 5-HT 4 receptor agonists," Bioorganic & Medicinal Chemistry 13:3295-3308 (2005).

International Search Report, issued Dec. 9, 2011 in connection with International Patent Application No. PCT/KR2011/002759, 6 pages.

Written Opinion, issued Dec. 9, 2011 in connection with International Patent Application No. PCT/KR2011/002759, 6 pages.

Office Action and translation, issued Dec. 27, 2011, in connection with Korean Patent Application No. KR 10-2010-0038039, 12 pages.

International Preliminary Report on Patentability, issued Jul. 5, 2012, with International Patent Application No. PCT/KR2011/002759, 5 pages.

Letter/Written Disclosure of the Supplemental Information Disclosure Statement for the above-referenced application, mailed on Jan. 24, 2014, 2 pages.

Clinical Trial: "The preventive effect of escitalopram on depression and related emotional disorders in acute stroke patients (EMOTION)" Dong-A Pharmaceutical Co., Ltd. first received Jan. 18, 2011; last updated Jun. 14, 2012 [online][retrieved on Jan. 21, 2014] Retrieved from:<URL:clinicaltrials.gov/ct2/show/NCT01278498?term=Dong-A&rank=25, 5 pages.

Office Action, issued Oct. 23, 2013, and translation, in connection with Russian Patent Application No. 2012150037/04 (080084), 7 pages.

Letter/Written Disclosure of the Supplemental Information Disclosure Statement for the above-referenced application, mailed on Sep. 3, 2015, 2 pages.

Examiner's Report, issued Aug. 1, 2013, in connection with Canadian Patent Application No. 2,794,176, 3 pages.

Response to Examiner's Report, submitted Jan. 28, 2014, in connection with Canadian Patent Application No. 2,794,176, 31 pages.

Examiner's Report, issued Apr. 24, 2014, in connection with Canadian Patent Application No. 2,794,176, 2 pages.

Standard Patent Notice of Grant, issued Oct. 30, 2014, in connection with Australian Patent Application No. 2011243393, 1 page.

Response to Examiner's Report, submitted Feb. 10, 2015, in connection with Canadian Patent Application No. 2,794,176, 30 pages.

Communication pursuant to Article 94(3), issued Aug. 14, 2015, in connection with European Patent Application No. 11 772 189.4, 3 pages.

Letter/Written Disclosure of the Supplemental Information Disclosure Statement for the above-referenced application, submitted on Apr. 10, 2015, 2 pages.

Communication pursuant to Article 94(3), issued Mar. 12, 2015, in connection with European Patent Application No. 11 772 189.4, 3 pages.

\* cited by examiner

BENZAMIDE DERIVATIVES

RELATED APPLICATIONS

This application is the National Stage of International Application. No. PCT/KR2011/002759, filed 18 Apr. 2011, which claims benefit of priority to KR-10-2010-0038039, filed 23 Apr. 2010, the specification of which is incorporated by reference herein.

TECHNICAL FIELD

The present invention relates to a novel benzamide derivative of formula 1 which will be illustrated hereinafter or a pharmaceutically acceptable salt thereof, a method for preparing the same, and a 5-$HT_4$ receptor agonist containing the same as an active ingredient.

BACKGROUND ART

Serotonin (5-HT) is a neurotransmitter widely distributed throughout the body. Seven subtypes of serotonin are currently known. In particular, great attention has been focused on the elucidation of a 5-$HT_4$ receptor and the confirmation of pharmaceutical action thereof.

In general, 5-$HT_4$ receptor agonists are found to be therapeutically effective for the treatment of various disease conditions such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive impairment, emesis, migraine, neurological disease, pain, cardiovascular disorder, cardiac failure, cardiac arrhythmia, diabetes and apnea syndrome (See Tips, 1992, 13, 141; Ford A. P. D. W. et al., *Med. Res. Rev.*, 1993, 13. 633; Gullikson G. W. et al., *Drug Dev. Res.*, 1992, 26, 405; Richard M. Eglen et al., *Tips*, 1995, 16, 391; Bockaert J. et al., *CNS Drugs*, 1, 6; Romanelli M. N. et al., *Arzheim Forsch./Drug Res.*, 1993, 43, 913; Kaumann A. et al., *Naunyn-Schmiedeberg's.* 1991, 344, 150; and Romanelli M. N. et al., *Arzheim Forsch./Drug Res.*, 1993, 43, 913).

Despite extensive uses of 5-$HT_4$ receptor agonists, there are little 5-$HT_4$ receptor agonist compounds that are currently clinically used. To this end, there is a need for a 5-$HT_4$ receptor agonist which is capable of exhibiting excellent medicinal effects while having minimum adverse side effects.

Benzamide derivatives have several prominent pharmacological actions. These excellent pharmacological activities of the benzamide derivatives are due to their effects on the nervous system which is controlled by serotonin that is a neurotransmitter. The role of serotonin, that is, the pharmacological action of benzamide derivatives has been broadly involved in a variety of diseases and conditions for many years. Further, a great deal of study and research has focused on production and storage sites of serotonin as well as the location of serotonin receptors in order to determine the relationship between the location of serotonin receptors and various disease states or conditions in humans.

Cisapride, which is a typical 5-$HT_4$ receptor agonist, is one of benzamide derivatives. U.S. Pat. Nos. 4,962,115, 5,057,525 and 5,137,896 disclose N-(3-hydroxy-4-piperidinyl)benzamides including cisapride. These compounds are known to stimulate gastrointestinal motility. Further, U.S. Pat. No. 5,864,039 discloses benzamide derivatives.

To this end, the inventors of the present invention succeeded in the synthesis of novel benzamide derivatives which exhibit an agonistic activity via strong binding with a 5-$HT_4$ receptor and good gastrointestinal absorption and which are capable of minimizing adverse side effects. The present invention has been completed based on this finding.

DISCLOSURE OF INVENTION

Technical Problem

The present invention is intended to provide a novel benzamide derivative or a pharmaceutically acceptable salt thereof and a method for preparing the same.

Further, the present invention is intended to provide a 5-$HT_4$ receptor agonist containing a novel benzamide derivative or a pharmaceutically acceptable salt thereof or a hydrate thereof as an active ingredient.

Solution to Problem

The present invention provides a novel benzamide derivative represented by formula 1 (a compound represented by formula 1):

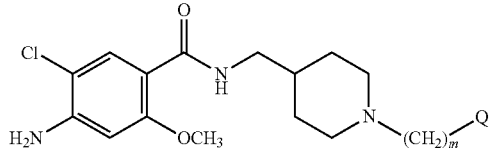

[Formula 1]

wherein m represents an integer of 1 to 10; and Q represents a heteroaromatic ring or phenyl, wherein the heteroaromatic ring or phenyl is independently substituted by 0, 1, 2, or 3 substituents selected from alkyl, alkoxy, hydroxy, cyano, nitro and halogen; or a pharmaceutically acceptable salt thereof.

Unless otherwise indicated, the following terms will have the following meanings throughout this specification.

As used herein, the term "alkyl" refers to a linear or branched, monovalent saturated $C_1$-$C_{20}$ hydrocarbon radical containing only carbon atoms and hydrogen atoms. Examples of the alkyl radical include methyl, ethyl, propyl, isopropyl, 2,2-dimethylpropyl, butyl, isobutyl, sec-butyl, tert-butyl, 3-methylbutyl, pentyl, 3-methylpentyl, 4-methylpentyl, n-hexyl, 2-ethylhexyl, octyl, and dodecyl.

As used herein, the term "alkoxy" refers to a radical —OR wherein R represents alkyl as defined above. Examples of the alkoxy radical include methoxy, ethoxy, propoxy, isopropoxy, butoxy, isobutoxy, sec-butoxy, tert-butoxy, pentoxy, 3-methylpentoxy, 4-methylpentoxy, n-hexoxy, and 2-ethylhexoxy.

As used herein, the term "heteroaromatic ring" refers to an aromatic ring or bicyclic aromatic ring contains 1 to 4 hetero atoms selected from O, N or S. Examples of the heteroaromatic ring include pyrrole, imidazole, triazole, tetrazole, pyridine, pyrimidine, oxazole, oxadiazole, isoxazole, indole, quinoline and benzofuran.

Further, the present invention provides a novel benzamide derivative represented by formula 1 wherein m represents an integer of 1 to 5; and Q represents a heteroaromatic ring or phenyl wherein the heteroaromatic ring or phenyl is independently substituted by 0, 1, 2 or 3 substituents selected from $C_1$-$C_4$ alkyl, $C_1$-$C_4$ alkoxy, hydroxy and halogen, wherein the heteroaromatic ring being a $C_1$-$C_{12}$ aromatic ring or $C_1$-$C_{12}$ bicyclic aromatic ring independently contains 1 to 4 hetero atoms selected from N, O or S; or a pharmaceutically acceptable salt thereof.

In the present invention, the pharmaceutically acceptable salt may be an acid addition salt with an acceptable free acid. The free acid may be an inorganic or organic acid. Examples of the inorganic acid include hydrochloric acid, hydrobromic acid, sulfuric acid, and phosphoric acid. Examples of the organic acid include citric acid, acetic acid, lactic acid, maleic acid, fumaric acid, gluconic acid, methanesulfonic acid, glycolic acid, succinic acid, 4-toluenesulfonic acid, trifluoroacetic acid, galacturonic acid, embonic acid, glutamic acid, and aspartic acid.

Further, the compound of formula 1 or a pharmaceutically acceptable salt thereof may exhibit polymorphism and may also be present in the form of a solvate (e.g., hydrate, etc).

Further, the present invention relates to a novel benzamide derivative selected from the group consisting of the following compounds:

(1) N-((1-(3-(1,2,4-triazol-1-yl)propyl)piperidin-4-yl)methyl)-4-amino-5-chloro-2-methoxybenzamide,
(2) N-((1-(3-(tetrazol-1-yl)propyl)piperidin-4-yl)methyl)-4-amino-5-chloro-2-methoxybenzamide,
(3) N-((1-(3-(indol-1-yl)propyl)piperidin-4-yl)methyl)-4-amino-5-chloro-2-methoxybenzamide,
(4) N-((1-(3-(2-methylimidazol-1-yl)propyl)piperidin-4-yl)methyl)-4-amino-5-chloro-2-methoxybenzamide,
(5) N-((1-(5-(indol-1-yl)pentyl)piperidin-4-yl)methyl)-4-amino-5-chloro-2-methoxybenzamide,
(6) N-((1-(5-(1,2,3-triazol-1-yl)pentyl)piperidin-4-yl)methyl)-4-amino-5-chloro-2-methoxybenzamide,
(7) N-((1-(3-(1,2,3-triazol-1-yl)propyl)piperidin-4-yl)methyl)-4-amino-5-chloro-2-methoxybenzamide,
(8) N-((1-(3-(1,2,3-triazol-2-yl)propyl)piperidin-4-yl)methyl)-4-amino-5-chloro-2-methoxybenzamide,
(9) N-((1-(pyridin-3-ylmethyl)piperidin-4-yl)methyl)-4-amino-5-chloro-2-methoxybenzamide,
(10) N-((1-((1-methylindol-3-yl)methyl)piperidin-4-yl)methyl)-4-amino-5-chloro-2-methoxybenzamide,
(11) N-((1-(imidazol-2-ylmethyl)piperidin-4-yl)methyl)-4-amino-5-chloro-2-methoxybenzamide,
(12) N-((1-((1-methylpyrrol-2-yl)methyl)piperidin-4-yl)methyl)-4-amino-5-chloro-2-methoxybenzamide,
(13) N-((1-(4-fluorobenzyl)piperidin-4-yl)methyl)-4-amino-5-chloro-2-methoxybenzamide,
(14) N-((1-(4-hydroxybenzyl)piperidin-4-yl)methyl)-4-amino-5-chloro-2-methoxybenzamide,
(15) N-((1-(2-(indol-3-yl)ethyl)piperidin-4-yl)methyl)-4-amino-5-chloro-2-methoxybenzamide,
(16) N-((1-(3-(tetrazol-1-yl)propyl)piperidin-4-yl)methyl)-4-amino-5-chloro-2-methoxybenzamide hydrochloride,
(17) N-((1-(5-(1,2,3-triazol-1-yl)pentyl)piperidin-4-yl)methyl)-4-amino-5-chloro-2-methoxybenzamide hydrochloride,
(18) N-((1-(3-(1,2,3-triazol-1-yl)propyl)piperidin-4-yl)methyl)-4-amino-5-chloro-2-methoxybenzamide hydrochloride,
(19) N-((1-((1-methylindol-3-yl)methyl)piperidin-4-yl)methyl)-4-amino-5-chloro-2-methoxybenzamide hydrochloride,
(20) N-((1-(4-fluorobenzyl)piperidin-4-yl)methyl)-4-amino-5-chloro-2-methoxybenzamide hydrochloride,
(21) N-((1-(4-hydroxybenzyl)piperidin-4-yl)methyl)-4-amino-5-chloro-2-methoxybenzamide hydrochloride and a pharmaceutically acceptable salt thereof.

Further, the present invention provides a method for preparing a benzamide derivative of formula 1 or a pharmaceutically acceptable salt thereof.

The present invention provides a method for preparing a compound of formula 1 or a pharmaceutically acceptable salt thereof, which includes reacting a compound of formula 2 or a pharmaceutically acceptable salt thereof with a compound of formula 3 in the presence of a base to introduce the compound of formula 3 at an amine of the 1-position of the piperidine ring of the compound of formula 2 or the pharmaceutically acceptable salt thereof, thereby preparing the compound of formula 1 (hereinafter, referred to as "Preparation Method 1").

[Formula 1]

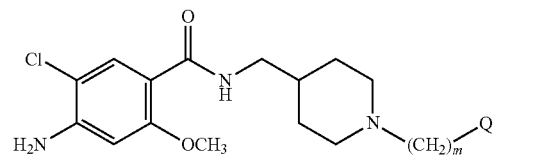

[Formula 2]

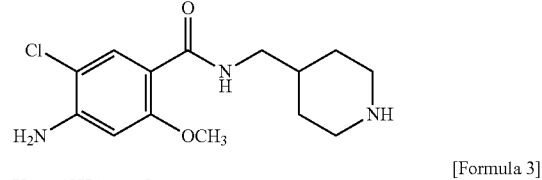

[Formula 3]

In the above formulae, m and Q are as defined in formula 1, and Y represents a halogen atom or $C_1$-$C_4$ alkylsulfonate.

In Preparation Method 1 of the present invention, the base is preferably selected from potassium carbonate, potassium iodide, triethylamine, diisopropylethylamine and their mixture, the solvent may be dimethylformamide, dimethylacetamide, acetone, 1,4-dioxane or the like, and the reaction may be carried out at a temperature of 50° C. to 140° C.

The present invention provides a method for preparing a compound of formula 1 or a pharmaceutically acceptable salt thereof, which includes reacting a compound of formula 2 or a pharmaceutically acceptable salt thereof with a compound of formula 11 in the presence of a reducing agent to prepare the compound of formula 1 (hereinafter, referred to as "Preparation Method 2").

[Formula 1]

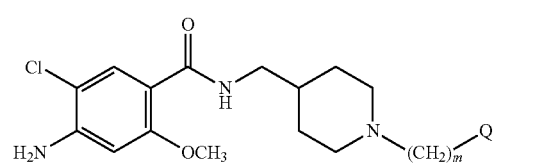

[Formula 2]

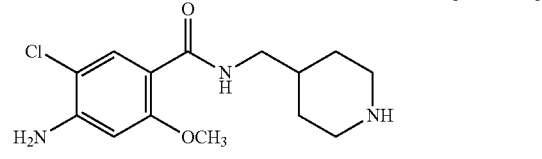

-continued

[Formula 11]

In the above formulae, Q is as defined in formula 1, and m represents an integer of 1.

In Preparation Method 2 of the present invention, the reducing agent is preferably sodium cyanoborohydride and acetic acid, or sodium borohydride, the solvent may be a $C_1$-$C_6$ lower alcohol, preferably ethanol or methanol, and the reaction may be carried out at a temperature of 50° C. to 100° C.

The compound of formula 2 or the pharmaceutically acceptable salt thereof in Preparation Method 1 or Preparation Method 2 of the present invention may be prepared by the following steps of:

(1) reacting a compound of formula 4 with an amine protecting group-introducing reagent to introduce an amine protecting group at an amine of the 1-position of the piperidine ring of the compound of formula 4, thereby obtaining a compound of formula 5;

(2) reacting hydroxy of the compound of formula 5 with N-bromosuccinimide and carbon tetrabromide, or with $C_1$-$C_4$ alkyl sulfonyl halide in the presence of a base to obtain a compound of formula 6;

(3) reacting a substituent Y of the compound of formula 6 with sodium azide to obtain a compound of formula 7;

(4) reducing the azido substituent of the compound of formula 7 into an amine in the presence of a reducing agent to obtain a compound of formula 8;

(5) reacting the compound of formula 8 with a compound of formula 9 in the presence of an amide bond formation-inducing reagent to obtain a compound of formula 10; and (6) deprotecting the amine protecting group of the piperidine ring of the compound of formula 10 in the presence of a base or acid.

[Formula 2]

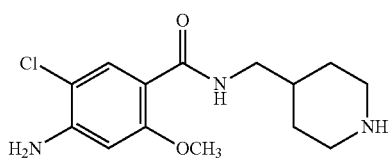

[Formula 4]

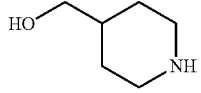

[Formula 5]

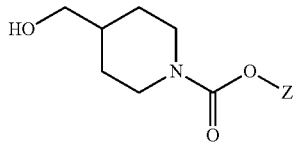

[Formula 6]

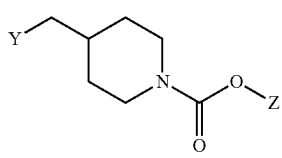

[Formula 7]

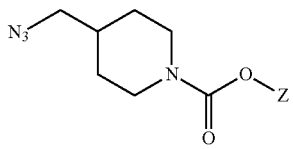

[Formula 8]

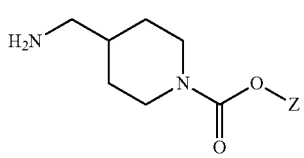

[Formula 9]

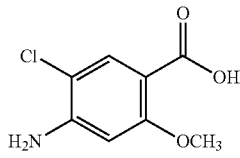

[Formula 10]

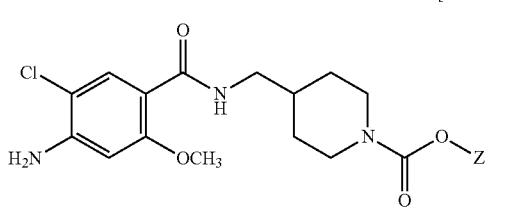

In the above formulae, Y represents a halogen atom or $C_1$-$C_4$ alkylsulfonate, and Z represents $C_1$-$C_4$ alkyl.

In the method for preparing a compound of formula 2 in accordance with the present invention, the amine protecting group-introducing reagent of Step (1) refers to a reagent used conventionally for the protection of an amine in order to prevent an amine group from participating in the reaction. For example, such a reagent is preferably selected from di-t-butyl dicarbonate or ethyl chloroformate in the presence of a tertiary amine such as triethylamine. The solvent may be a $C_1$-$C_6$ lower alcohol. The reaction may be carried out with gradual elevation of a temperature from 0° C. to room temperature.

In the method for preparing a compound of formula 2 in accordance with the present invention, the $C_1$-$C_4$ alkyl sulfonyl halide of Step (2) is preferably methane sulfonyl chloride, methane sulfonyl bromide or methane sulfonyl fluoride, the tertiary amine may be triethylamine, diisopropylethylamine or the like, and the solvent may be dichloromethane, chloroform, or the like. The reaction may be carried out with gradual elevation of a temperature from 0° C. to room temperature.

In the method for preparing a compound of formula 2 in accordance with the present invention, the solvent used in Step (3) may be dimethylformamide, dimethylacetamide or the like, and the reaction temperature may be in the range of 80 to 140° C.

In the method for preparing a compound of formula 2 in accordance with the present invention, the reducing agent used in Step (4) is preferably triphenylphosphine or lithium aluminum hydride, and the solvent used may be tetrahydrofuran. The reaction may be carried out with gradual elevation of a temperature from 0° C. to room temperature or may be carried out in the range of 60 to 80° C.

In the method for preparing a compound of formula 2 in accordance with the present invention, the amide bond formation-inducing reagent used in Step (5) refers to a common reagent which is used by a person of ordinary skill and which is used to remove water generated after the reaction, in order to promote the amide bond between carboxylic acid and an amine, or is used to activate an amine or carboxylic acid. Examples of the amide bond formation-inducing reagent include N-(3-dimethylaminopropyl)-N'-ethylcarbodiimide hydrochloride and 1-hydroxybenzotriazole in the presence of a base, ethyl chloroformate in the presence of a base, and carbodiimidazole in the absence of a base. Here, examples of the base used in combination with N-(3-dimethylaminopropyl)-N'-ethylcarbodiimide hydrochloride and 1-hydroxybenzotriazole, or ethyl chloroformate include triethylamine and diisopropylethylamine. Here, the reaction solvent used may be dimethyl formamide, dimethyl acetamide, dichloromethane, or the like. The reaction may be carried out with gradual elevation of a temperature from 0° C. to room temperature.

In the method for preparing a compound of formula 2 in accordance with the present invention, the base or acid of Step (6) refers to a base or acid which is conventionally used to deprotect the carbamate of an amine, and examples thereof include hydrochloric acid, trifluoroacetic acid, and potassium hydroxide. The reaction solvent used may be 1,4-dioxane, dichloromethane, $C_1$-$C_6$ lower alcohol, or the like. The reaction may be carried out with gradual elevation of a temperature from 0° C. to room temperature.

The compound of formula 3 in the present invention may be prepared according to the method as in Reaction Scheme 1 or Reaction Scheme 2 provided below.

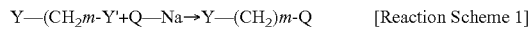

[Reaction Scheme 1]

In Reaction Scheme 1, the substituents Q and m are as defined in formula 1, and both of Y and Y' represent halogen atoms which are preferably different from each other, for example, one of Y and Y' represents chloro (Cl) and the other one of Y and Y' represents bromo (Br).

The reaction of Reaction Scheme 1 may be carried out in the presence of a strong base such as lithium hydride, sodium hydride or potassium hydride, in an organic solvent such as dimethylformamide, dimethylacetamide or tetrahydrofuran, at a reaction temperature of 0 to 40° C. for 1 to 24 hours.

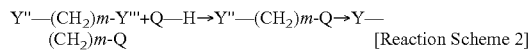

[Reaction Scheme 2]

In Reaction Scheme 2, the substituents Q and m are as defined in formula 1, Y represents a $C_1$-$C_4$ alkyl sulfonyl halide or a halogen atom, Y" represents a hydroxyl group, and Y''' represents a halogen atom selected from Cl, Br or I.

The first step reaction of Reaction Scheme 2 may be carried out in the presence of a base such as potassium carbonate and potassium iodide, in a solvent such as 1,4-dioxane or acetone, at a temperature of 60 to 120° C. for 1 to 12 hours.

When Y of formula 3 represents a $C_1$-$C_4$ alkyl sulfonyl halide, the second step reaction of Reaction Scheme 2 may be carried out by reacting Y"—(CH$_2$)m-Q with a $C_1$-$C_4$ alkyl sulfonyl halide (for example, methane sulfonyl chloride, methane sulfonyl bromide, or methane sulfonyl fluoride) in the presence of a base such as triethylamine or diisopropylethylamine, in an organic solvent such as dichloromethane or chloroform, at a reaction temperature of 0 to 40° C. for 1 to 24 hours.

When the substituent Y of formula 3 represents a halogen atom, the second step reaction of Reaction Scheme 2 may be carried out under the conventionally known reaction conditions for substitution of the hydroxyl group of with a halogen. For example, when the substituent Y of Y"—(CH$_2$)m-Q with a halogen. For example, when the substituent Y of formula 3 represents bromo (Br), the reaction may be carried out in the presence of one species selected from N-bromosuccinimide or carbon tetrabromide and triphenylphosphine, in an organic solvent such as dichloromethane, at a reaction temperature of 0 to 40° C. for 1 to 24 hours.

The acid addition salt of a free base of a compound represented by formula 1 may be prepared using a conventional method known in the art, for example by mixing a free base of the compound of formula 1 with an appropriate acid in a suitable solvent, which is then followed by evaporation to form a salt or the addition of a non-solvent to precipitate a salt. For example, mention may be made of a method which involves treating a solution or suspension of a free base with a desired acid in a reaction-inert solvent, followed by concentration under reduced pressure or crystallization or any standard chemical manipulation to form a desired salt. In one embodiment, a hydrochloride of the compound of formula 1 may be prepared by dissolving a free base of the compound of formula 1 in a $C_1$-$C_4$ alcohol solvent such as ethanol or methanol, adding hydrochloric acid thereto, and then stirring the mixture at room temperature.

Further, the present invention provides a 5-HT$_4$ receptor agonist containing a compound of formula 1 or a pharmaceutically acceptable salt thereof or a hydrate thereof as an active ingredient.

In the present invention, the 5-HT$_4$ receptor agonist may be a composition for the prevention or treatment of a disease selected from gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive impairment, emesis, migraine, neurological disease, pain, cardiovascular disorder, cardiac failure, cardiac arrhythmia, diabetes or apnea syndrome.

In the present invention, the 5-HT$_4$ receptor agonist of the present invention may further contain one or more active ingredients exhibiting an identical or similar function, in addition to the compound of formula 1 in accordance with the present invention or a pharmaceutically acceptable salt thereof.

For the purpose of desired administration, the agonist or composition of the present invention may be formulated into a variety of dosage forms by further inclusion of one or more pharmaceutically acceptable carriers in combination with the above-mentioned active ingredient. Examples of the pharmaceutically acceptable carrier include saline, sterile water, Ringer's solution, buffered saline, a dextrose solution, a maltodextrin solution, glycerol, and ethanol. These materials may be used alone or in any combination thereof. If necessary, other conventional additives may be added such as an antioxidant, a buffer and a bacteriostatic agent. Further, a diluent, a dispersant, a surfactant, a binder and a lubricant may be additionally added to prepare an injectable formulation such as aqueous solution, suspension or emulsion, or an oral formulation such as pill, capsule, granule or tablet. Furthermore, the desired dosage form may be preferably formulated depending on diseases to be treated and ingredients, using any appropriate method known in the art, as disclosed in "Remington's Pharmaceutical Sciences, Mack Publishing Co., Easton, Pa.

Further, when the 5-HT$_4$ receptor agonist of the present invention is intended for oral administration, the content of the compound of formula 1 in accordance with the present invention or a pharmaceutically acceptable salt thereof in the formulation may be in the range of 1 to 95% by weight and preferably 1 to 70% by weight.

The agonist or composition of the present invention may be administered parenterally (for example, intravenously, subcutaneously, intraperitoneally or locally) or orally, depending on desired applications. The dose of the active ingredient may vary depending on various factors such as weight, age, sex, health status and dietary habits of patients, administration times and routes, excretion rates, and severity of diseases. The benzamide derivative of the present invention may be administered at a dose of 1 to 1000 μg/kg, preferably about 10 to 500 μg/kg and more preferably about 83 to 167 μg/kg, once or several times a day.

Further, the present invention provides a method for the prevention, treatment or alleviation of a disease due to attenuated efficacy of a 5-HT$_4$ receptor, including administering a 5-HT$_4$ receptor agonist containing a compound of formula 1 in accordance with the present invention or a pharmaceutically acceptable salt thereof as an active ingredient to a mammal including a human in need of 5-HT$_4$ receptor agonistic effects. Here, the 5-HT$_4$ receptor agonist may be a composition for the prevention or treatment of a disease selected from gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive impairment, emesis, migraine, neurological disease, pain, cardiovascular disorder, cardiac failure, cardiac arrhythmia, diabetes or apnea syndrome.

For the prevention and treatment of a disease due to attenuated efficacy of a 5-HT$_4$ receptor, the 5-HT$_4$ receptor agonist of the present invention may be used alone or in combination with methods employing surgical operation, hormone therapy, medication therapy and biological response modifiers.

Advantageous Effects of Invention

Benzamide derivatives of the present invention have a superior affinity for 5-HT$_4$ receptors, a capability to reduce a gastric emptying time and a low toxicity, and consequently are therapeutically effective for the treatment of a variety of diseases associated with 5-HT$_4$ receptors.

MODE FOR THE INVENTION

Hereinafter, the present invention will be described in more detail with reference to the following Examples. However, the following Examples are provided only for illustrating the present invention and should not be construed as limiting the scope and spirit of the present invention.

Unless otherwise indicated, reagents used hereinafter were purchased from Aldrich Korea, Acros, Lancaster, TCI, etc., and $^1$H NMR experiments were performed using a Varian 400 MHz spectrometer.

Example 1

Preparation of N-((1-(3-(1,2,4-triazol-1-yl)propyl) piperidin-4-yl)methyl)-4-amino-5-chloro-2-methoxybenzamide 1-1. Preparation of 4-amino-5-chloro-2-methoxy-(piperidin-4-ylmethyl) benzamide (Compound of Formula 2) Hydrochloride Step 1: Preparation of tertiary butyl 4-(hydroxymethyl)piperidine-1-carboxylate (Compound of Formula 5)

4-piperidine methanol (compound of formula 4) (20 g, 174 mmol) was dissolved in methanol (30 mL) and the solution was cooled to 0° C. Then, triethylamine (48.8 mL, 347 mmol) and di-tertiary-butyl dicarbonate (56.8 g, 260 mmol) were added thereto. The reaction mixture was warmed to room temperature, stirred for 2 hours, and concentrated under reduced pressure to remove the solvent. After extraction with dichloromethane and water, the organic layer was washed with a citric acid solution, dried over anhydrous magnesium sulfate and concentrated under reduced pressure to afford the title compound (35.25 g, 94%).

$^1$H NMR (CDCl$_3$, 400 MHz): δ4.18-4.04 (m, 2H), 3.47 (t, J=5.6 Hz, 2H), 2.70-2.64 (m, 2H), 1.70-1.56 (m, 3H), 1.42 (s, 9H), 1.16-1.09 (m, 2H).

Step 2: Preparation of Tertiary Butyl 4-((methylsulfonyloxy)methyl) piperidine-1-carboxylate (Compound of Formula 6)

Tertiary butyl 4-(hydroxymethyl)piperidine-1-carboxylate (35.25 g, 164 mmol) was dissolved in dichloromethane (300 mL) and the solution was cooled to 0° C. Then, triethylamine (46.01 mL, 327 mmol) and methane sulfonyl chloride (19.14 mL, 246 mmol) were added thereto. The reaction mixture was warmed to room temperature, stirred for 2 hours, and extracted with dichloromethane and water. The organic layer was washed with a citric acid solution, dried over anhydrous magnesium sulfate and concentrated under reduced pressure to afford the title compound (48 g, 100%).

$^1$H NMR (CDCl$_3$, 400 MHz): δ4.18-4.06 (m, 2H), 4.04 (d, J=6.4 Hz, 2H), 2.99 (s, 3H), 2.78-2.62 (m, 2H), 1.92-1.85 (m, 1H), 1.73-1.70 (m, 2H), 1.43 (s, 9H), 1.24-1.13 (m, 2H).

Step 3: Preparation of Tertiary Butyl 4-(azidomethyl)piperidine-1-carboxylate (Compound of Formula 7)

Tertiary butyl 4-((methylsulfonyloxy)methyl)piperidine-1-carboxylate (48 g, 163.6 mmol) was dissolved in dimethylformamide (500 mL) and sodium azide (19.15 g, 295 mmol) was added thereto, followed by stirring at 120° C. for 6 hours. After the reaction was completed, the reactants were cooled to room temperature, extracted with ethyl acetate and water, dried over anhydrous magnesium sulfate, and concentrated under reduced pressure to afford the title compound (35 g, 89%).

$^1$H NMR (CDCl$_3$, 400 MHz): δ4.18-4.00 (m, 2H), 3.16 (d, J=6.0 Hz, 2H), 2.72-2.58 (m, 2H), 1.70-1.64 (m, 3H), 1.43 (s, 9H), 1.20-1.08 (m, 2H).

Step 4: Preparation of Tertiary Butyl 4-(aminomethyl)piperidine-1-carboxylate (Compound of Formula 8)

Tertiary butyl 4-(azidomethyl)piperidine-1-carboxylate (30 g, 124.8 mmol) was dissolved in tetrahydrofuran (300 mL), and triphenylphosphine (39.3 g, 149.8 mmol) was added thereto, followed by stirring under reflux for 2 hours. Water (120 mL) was added thereto, followed by stirring under reflux for another 3 hours and concentration under reduced pressure. The resulting residue was extracted with ethyl acetate and a 1N hydrochloride solution, and the aqueous layer was neutralized with a 2N sodium hydroxide solution, followed by re-extraction with dichloromethane. The resulting organic layer was dried over anhydrous magnesium sulfate and concentrated under reduced pressure to afford the title compound (21.16 g, 79%).

¹H NMR (CDCl₃, 400 MHz): δ4.16-3.98 (m, 2H), 2.69-2.63 (m, 2H), 2.56 (d, J=6.8 Hz, 2H), 1.69-1.66 (m, 2H), 1.46-1.38 (m, 10H), 1.10-1.04 (m, 2H).

Step 5: Preparation of Tertiary Butyl 4-((4-amino-5-chloro-2-methoxybenzamido)methyl)piperidine-1-carboxylate (Compound of Formula 10)

4-amino-5-chloro-2-methoxybenzoic acid (compound of formula 9) (16.6 g, 82.28 mmol) was dissolved in dimethylformamide (166 mL) and the solution was cooled to 0° C. Then, tertiary butyl 4-(aminomethyl)piperidine-1-carboxylate (21.16 g, 98.74 mmol), triethylamine (11.56 mL, 246.84 mmol), N-(3-dimethylaminopropyl)-N'-ethylcarbodiimide hydrochloride (EDC, 20.51 g, 106.96 mmol), and 1-hydroxybenzotriazole (HOBT, 16.68 g, 123.42 mmol) were added thereto. The reaction mixture was warmed to room temperature, stirred for 4 hours, and extracted with ethyl acetate and water. The organic layer was dried over anhydrous magnesium sulfate and concentrated under reduced pressure to afford the title compound (31.4 g, 96%).
¹H NMR (CDCl₃, 400 MHz): δ8.08 (s, 1H), 7.76-7.70 (m, 1H), 6.27 (s, 1H), 4.37 (s, 2H), 4.16-4.04 (m, 2H), 3.88 (s, 3H), 3.34-3.26 (m, 2H), 2.74-2.60 (m, 2H), 1.80-1.63 (m, 3H), 1.42 (s, 9H), 1.20-1.10 (m, 2H).

Step 6: Preparation of 4-amino-5-chloro-2-methoxy-(piperidin-4-ylmethyl)benzamide (Compound of Formula 2) Hydrochloride Tertiary butyl 4-((4-amino-5-chloro-2-methoxybenzamido)methyl)piperidine-1-carboxylate (30.7 g, 77.16 mmol) was dissolved in 1,4-dioxane (300 mL), and a 4M hydrochloride solution (220 mL) in 1,4-dioxane was added thereto. The mixture was stirred at room temperature for 2 hours and concentrated under reduced pressure to afford the title compound (24 g, 93%).
¹H NMR (CD₃OD, 400 MHz): δ7.84 (s, 1H), 6.84 (s, 1H), 3.95 (s, 3H), 3.42-3.29 (m, 6H), 3.01-2.95 (m, 2H), 1.98-1.93 (m, 3H), 1.54-1.42 (m, 2H).

1-2. Preparation of 1-(3-chloropropyl)-1,2,4-triazole (Compound of Formula 3)

A 1,2,4-triazole sodium salt (5 g, 54.91 mmol) was dissolved in dimethylformamide (50 mL) and the solution was cooled to 0° C. Then, sodium hydride (60%, 2.86 g, 71.38 mmol) was added thereto, followed by stirring for 30 minutes. 1-bromo-3-chloropropane (6.5 mL, 65.89 mmol) was added thereto, followed by stirring at room temperature for 12 hours, and the reaction was terminated with the addition of an ammonium chloride saturated solution. After extraction with ethyl acetate and water, the organic layer was washed with brine, dried over anhydrous magnesium sulfate and concentrated under reduced pressure. The resulting residue was purified by column chromatography to afford the title compound (2.77 g, 35%).
¹H NMR (CDCl₃, 400 MHz): δ8.08 (s, 1H), 7.94 (s, 1H), 4.36 (t, J=6.4 Hz, 2H), 3.45 (t, J=6 Hz, 2H), 2.35-2.30 (m, 2H).

1-3: Preparation of N-((1-(3-(1,2,4-triazol-1-yl)propyl)piperidin-4-yl)methyl)-4-amino-5-chloro-2-methoxybenzamide (Compound of Formula 1)

4-amino-5-chloro-2-methoxy-(piperidin-4-ylmethyl)benzamide (compound of formula 2) hydrochloride (500 mg, 1.5 mmol) was dissolved in dimethylformamide (10 mL), and 1-(3-chloropropyl)-1,2,4-triazole (compound of formula 3) (306 mg, 2.1 mmol), potassium carbonate (497 mg, 3.6 mmol), and potassium iodide (50 mg, 0.3 mmol) were added thereto. The reactants were stirred at 100° C. for 8 hours, and the reaction was terminated with the addition of water. After extraction with ethyl acetate and water, the organic layer was washed with brine, dried over anhydrous magnesium sulfate and concentrated under reduced pressure. The resulting residue was purified by column chromatography to afford the title compound (55 mg, 9%).
¹H NMR (CDCl₃, 400 MHz): δ8.09 (s, 1H), 8.04 (s, 1H), 7.91 (s, 1H), 7.78-7.70 (m, 1H), 6.27 (s, 1H), 4.35 (s, 2H), 4.22 (t, J=6.4 Hz, 2H), 3.88 (s, 3H), 3.30 (t, J=6.4 Hz, 2H), 2.85-2.81 (m, 2H), 2.24 (t, J=6.4 Hz, 2H), 2.06-2.00 (m, 2H), 1.97-1.90 (m, 2H), 1.78-1.50 (m, 3H), 1.39-1.28 (m, 2H).

Example 2

Preparation of N-((1-(3-(tetrazol-1-yl)propyl)piperidin-4-yl)methyl)-4-amino-5-chloro-2-methoxybenzamide 1-(3-chloropropyl)-tetrazole was prepared using 1H-tetrazole and 1-bromo-3-chloropropane as starting materials of <Example 1-2>, and then the title compound (186 mg) was obtained using 1-(3-chloropropyl)-tetrazole and 4-amino-5-chloro-2-methoxy-(piperidin-4-ylmethyl)benzamide hydrochloride as starting materials of <Example 1-3>.
¹H NMR (CDCl₃, 400 MHz): δ8.60 (s, 1H), 8.07 (s, 1H), 7.75-7.68 (m, 1H), 6.28 (s, 1H), 4.49 (t, J=6.8 Hz, 2H), 4.39 (s, 2H), 3.88 (s, 3H), 3.30 (t, J=6.4 Hz, 2H), 2.79-2.76 (m, 2H), 2.23 (t, J=6.8 Hz, 2H), 2.10-2.05 (m, 2H), 1.92-1.86 (m, 2H), 1.75-1.69 (m, 2H), 1.62-1.50 (m, 1H), 1.35-1.23 (m, 2H).

Example 3

Preparation of N-((1-(3-(indol-1-yl)propyl)piperidin-4-yl)methyl)-4-amino-5-chloro-2-methoxybenzamide 1-(3-chloropropyl)-indole was prepared using indole and 1-bromo-3-chloropropane as starting materials of <Example 1-2>, and then the title compound (26 mg) was obtained using 1-(3-chloropropyl)-indole and 4-amino-5-chloro-2-methoxy-(piperidin-4-ylmethyl)benzamide hydrochloride as starting materials of <Example 1-3>.
¹H NMR (CDCl₃, 400 MHz): δ8.09 (s, 1H), 7.85-7.76 (m, 1H), 7.60 (d, J=7.6 Hz, 1H), 7.34 (d, J=8.0 Hz, 1H), 7.15 (t, J=7.2 Hz, 1H), 7.10-7.07 (m, 2H), 6.45 (d, J=3.2 Hz, 1H), 6.27 (s, 1H), 4.34 (s, 2H), 4.18 (t, J=7.2 Hz, 2H), 3.88 (s, 3H), 3.32 (t, J=6.4 Hz, 2H), 2.88-2.85 (m, 2H), 2.26 (t, J=7.2 Hz, 2H), 2.03-1.97 (m, 2H), 1.90-1.80 (m, 2H), 1.73-1.60 (m, 3H), 1.40-1.32 (m, 2H).

Example 4

Preparation of N-((1-(3-(2-methylimidazol-1-yl)propyl) piperidin-4-yl)methyl)-4-amino-5-chloro-2-methoxybenzamide 1-(3-chloropropyl)-2-methylimidazole was prepared using 2-methylimidazole and 1-bromo-3-chloropropane as starting materials of <Example 1-2>, and then the title compound (226 mg) was obtained using 1-(3-chloropropyl)-2- methylimidazole and 4-amino-5-chloro-2-methoxy-(piperidin-4-ylmethyl)benzamide hydrochloride as starting materials of <Example 1-3>.

$^1$H NMR (CDCl$_3$, 400 MHz): δ8.06 (s, 1H), 7.78-7.69 (m, 1H), 6.85 (s, 1H), 6.78 (s, 1H), 6.27 (s, 1H), 4.46 (s, 2H), 3.87-3.83 (m, 5H), 3.29 (t, J=6.0 Hz, 2H), 2.85-2.79 (m, 2H), 2.34 (s, 3H), 2.22 (t, J=6.8 Hz, 2H), 1.90-1.83 (m, 4H), 1.72-1.67 (m, 2H), 1.63-1.50 (m, 1H), 1.32-1.26 (m, 2H).

Example 5

Preparation of N-((1-(5-(indol-1-yl)pentyl)piperidin-4-yl)methyl)-4-amino-5-chloro-2-methoxybenzamide 1-(5-chloropentyl)-indole was prepared using indole and 1-bromo-5-chloropentane as starting materials of <Example 1-2>, and then the title compound (250 mg) was obtained using 1-(5-chloropentyl)-indole and 4-amino-5-chloro-2-methoxy-(piperidin-4-ylmethyl)benzamide hydrochloride as starting materials of <Example 1-3>.

$^1$H NMR (CDCl$_3$, 400 MHz): δ8.09 (s, 1H), 7.75-7.69 (m, 1H), 7.60 (d, J=8.0 Hz, 1H), 7.31 (d, J=7.6 Hz, 1H), 7.19-7.16 (m, 1H), 7.09-7.05 (m, 2H), 6.47-6.44 (m, 1H), 6.26 (s, 1H), 4.34 (s, 2H), 4.11-4.08 (m, 2H), 3.87 (s, 3H), 3.30 (t, J=6.0 Hz, 2H), 2.92-2.86 (m, 2H), 2.28-2.20 (m, 2H), 1.91-1.80 (m, 4H), 1.72-1.48 (m, 5H), 1.39-1.26 (m, 4H).

Example 6

Preparation of N-((1-(5-(1,2,3-triazol-1-yl)pentyl)piperidin-4-yl)methyl)-4-amino-5-chloro-2-methoxybenzamide 1-(5-chloropentyl)-1,2,3-triazole was prepared using 1,2,3-triazole and 1-bromo-5-chloropentane as starting materials of <Example 1-2>, and then the title compound (225 mg) was obtained using 1-(5-chloropentyl)-1,2,3-triazole and 4-amino-5-chloro-2-methoxy-(piperidin-4-ylmethyl)benzamide hydrochloride as starting materials of <Example 1-3>.

$^1$H NMR (CDCl$_3$, 400 MHz): δ8.06 (s, 1H), 7.79-7.70 (m, 1H), 7.67 (s, 1H), 7.52 (s, 1H), 6.27 (s, 1H), 4.41 (s, 2H), 4.35 (t, J=6.8 Hz, 2H), 3.86 (s, 3H), 3.28 (t, J=6.0 Hz, 2H), 2.92-2.88 (m, 2H), 2.28 (t, J=7.6 Hz, 2H), 1.94-1.84 (m, 4H), 1.72-1.68 (m, 2H), 1.66-1.46 (m, 3H), 1.34-1.21 (m, 4H).

Example 7

Preparation of N-((1-(3-(1,2,3-triazol-1-yl)propyl)piperidin-4-yl)methyl)-4-amino-5-chloro-2-methoxybenzamide Step 1: Preparation of 3-(1,2,3-triazol-1-yl)propanol 1,2,3-triazole (2 g, 28.96 mmol) was dissolved in 1,4-dioxane (40 mL), and potassium carbonate (8 g, 57.92 mmol), potassium iodide (962 mg, 5.79 mmol) and 3-bromopropanol (3.3 mL, 43.43 mmol) were added thereto, followed by stirring at 100° C. for 3 hours. After the reaction was completed, the reactants were cooled to room temperature and filtered. The filtrate was concentrated under reduced pressure. The resulting residue was purified by column chromatography to afford the title compound (2.5 g, 68%).

$^1$H NMR (CDCl$_3$, 400 MHz): δ7.68 (s, 1H), 7.59 (s, 1H), 4.54 (t, J=6.8 Hz, 2H), 3.62 (q, J=5.6 Hz, 2H), 2.44 (t, J=5.2 Hz, 1H), 2.15-2.10 (m, 2H).

Step 2: Preparation of 3-(1,2,3-triazol-1-yl)propyl methanesulfonate 3-(1,2,3-triazol-1-yl)propanol (2.5 g, 19.66 mmol) was dissolved in dichloromethane (50 mL), and the solution was cooled to 0° C. Then, triethylamine (5.53 mL, 39.32 mmol) and methane sulfonyl chloride (2.3 mL, 29.5 mmol) were added thereto. The reaction mixture was warmed to room temperature, stirred for 2 hours, extracted with dichloromethane and water, dried over anhydrous magnesium sulfate, and concentrated under reduced pressure. The resulting residue was purified by column chromatography to afford the title compound (3.01 g, 75%).

$^1$H NMR (CDCl$_3$, 400 MHz): δ7.72 (s, 1H), 7.63 (s, 1H), 4.55 (t, J=6.8 Hz, 2H), 4.22 (t, J=6 Hz, 2H), 3.03 (s, 3H), 2.40-2.36 (m, 2H).

Step 3: Preparation of N-((1-(3-(1,2,3-triazol-1-yl)propyl)piperidin-4-yl)methyl)-4-amino-5-chloro-2-methoxybenzamide 4-amino-5-chloro-2-methoxy-(piperidin-4-ylmethyl)benzamide (compound of formula 2) hydrochloride (400 mg, 1.2 mmol) was dissolved in dimethylformamide (10 mL), and 3-(1,2,3-triazol-1-yl)propyl methanesulfonate (compound of formula 3) (344 mg, 1.68 mmol), triethylamine (0.5 mL, 3.591 mmol), potassium carbonate (232 mg, 1.68 mmol), and potassium iodide (40 mg, 0.24 mmol) were added thereto, followed by stirring at 120° C. for 4 hours. After the reaction was completed, the reactants were cooled to room temperature, extracted with ethyl acetate and water, dried over anhydrous magnesium sulfate, and concentrated under reduced pressure. The resulting residue was purified by column chromatography to afford the title compound (185 mg, 38%).

$^1$H NMR (CDCl$_3$, 400 MHz): δ8.09 (s, 1H), 7.74-7.70 (m, 1H), 7.67 (s, 1H), 7.54 (s, 1H), 6.27 (s, 1H), 4.43 (t, J=6.8 Hz, 2H), 4.35 (s, 2H), 3.88 (s, 3H), 3.31 (t, J=6.4 Hz, 2H), 2.85-2.82 (m, 2H), 2.27 (t, J=6.8 Hz, 2H), 2.07-2.04 (m, 2H), 1.92-1.86 (m, 2H), 1.73-1.69 (m, 2H), 1.62-1.50 (m, 1H), 1.34-1.22 (m, 2H).

Example 8

Preparation of N-((1-(3-(1,2,3-triazol-2-yl)propyl)piperidin-4-yl)methyl)-4-amino-5-chloro-2-methoxybenzamide Using 3-(1,2,3-triazol-2-yl)propanol obtained as a by-product in Step 1 of Example 7 and 4-amino-5-chloro-2-methoxy-(piperidin-4-ylmethyl)benzamide hydrochloride as starting materials, the title compound (250 mg) was obtained in the same manner as in <Example 7>.

$^1$H NMR (CDCl$_3$, 400 MHz): δ8.03 (s, 1H), 7.83-7.75 (m, 1H), 7.53 (s, 2H), 6.25 (s, 1H), 4.50-4.42 (m, 4H), 3.82 (s, 3H), 3.26 (t, J=6.0 Hz, 2H), 2.86-2.83 (m, 2H), 2.31-2.27 (m, 2H), 2.12-2.05 (m, 2H), 1.89-1.83 (m, 2H), 1.67-1.64 (m, 2H), 1.60-1.50 (m, 1H), 1.31-1.20 (m, 2H).

Example 9

Preparation of N-((1-(pyridin-3-ylmethyl)piperidin-4-yl)methyl)-4-amino-5-chloro-2-methoxybenzamide 4-amino-5-chloro-2-methoxy-(piperidin-4-ylmethyl)benzamide hydrochloride (1 g, 2.99 mmol) was dissolved in methanol (40 mL), and 3-pyridine carboxaldehyde (0.42 mL, 4.49 mmol), acetic acid (1 mL) and sodium cyanoborohydride (470 mg, 7.48 mmol) were added thereto, followed by stirring at 60° C. for 5 hours. After the reaction was completed, the reaction mixture was concentrated under reduced pressure to remove the solvent, extracted with dichloromethane and water, and then washed with a sodium bicarbonate solution. The organic layer was dried over anhydrous magnesium sulfate and concentrated under reduced pressure. The resulting residue was purified by column chromatography to afford the title compound (355 mg, 30%).

$^1$H NMR (CDCl$_3$, 400 MHz): δ8.07 (s, 1H), 7.74-7.69 (m, 1H), 7.65 (d, J=7.6 Hz, 1H), 7.37 (s, 1H), 7.30 (d, J=8.4 Hz, 1H), 7.25-7.22 (m, 1H), 7.19-7.15 (m, 1H), 6.26 (s, 1H), 4.42 (s, 2H), 3.83 (s, 3H), 3.77 (s, 3H), 3.28 (t, J=5.6 Hz, 2H), 2.95-2.82 (m, 4H), 2.19-2.14 (m, 4H), 1.91-1.85 (m, 2H), 1.80-1.72 (m, 2H), 1.69-1.63 (m, 2H), 1.61-1.53 (m, 1H), 1.32-1.15 (m, 5H).

Example 10

Preparation of N-((1-((1-methylindol-3-yl)methyl) piperidin-4-yl)methyl)-4-amino-5-chloro-2-methoxybenzamide Using 1-methylindole-3-carboxaldehyde and 4-amino-5-chloro-2-methoxy-(piperidin-4-ylmethyl)benzamide hydrochloride as starting materials, the title compound (60 mg) was obtained in the same manner as in <Example 9>.

$^1$H NMR (CDCl$_3$, 400 MHz): δ8.02 (s, 1H), 7.82-7.75 (m, 1H), 7.56 (d, J=8.4 Hz, 1H), 7.33-7.22 (m, 3H), 7.12 (t, J=7.2 Hz, 1H), 6.27 (s, 1H), 4.38 (s, 2H), 4.01 (s, 2H), 3.87 (s, 3H), 3.79 (s, 3H), 3.30-3.23 (m, 2H), 2.46-2.37 (m, 2H), 1.88-1.75 (m, 3H), 1.59-1.50 (m, 2H).

Example 11

Preparation of N-((1-(imidazol-2-ylmethyl)piperidin-4-yl)methyl)-4-amino-5-chloro-2-methoxybenzamide Using 2-imidazole carboxaldehyde and 4-amino-5-chloro-2-methoxy-(piperidin-4-ylmethyl)benzamide hydrochloride as starting materials, the title compound (123 mg) was obtained in the same manner as in <Example 9>.

$^1$H NMR (CDCl$_3$, 400 MHz): δ8.07 (s, 1H), 7.75-7.66 (m, 1H), 6.96 (s, 2H), 6.27 (s, 1H), 4.38 (s, 2H), 3.87 (s, 3H), 3.61 (s, 2H), 3.31 (t, J=6.8 Hz, 2H), 2.85-2.80 (m, 2H), 2.11-2.04 (m, 2H), 1.74-1.69 (m, 2H), 1.63-1.53 (m, 1H), 1.34-1.23 (m, 2H).

Example 12

Preparation of N-((1-((1-methylpyrrol-2-yl)methyl) piperidin-4-yl)methyl)-4-amino-5-chloro-2-methoxybenzamide Using 1-methyl-2-pyrrole carboxaldehyde and 4-amino-5-chloro-2-methoxy-(piperidin-4-ylmethyl)benzamide hydrochloride as starting materials, the title compound (50 mg) was obtained in the same manner as in <Example 9>.

$^1$H NMR (CDCl$_3$, 400 MHz): δ8.08 (s, 1H), 7.75-7.64 (m, 1H), 6.57-6.53 (m, 1H), 6.26 (s, 1H), 6.00-5.96 (m, 1H), 5.95-5.93 (m, 1H), 4.38 (s, 2H), 3.85 (s, 3H), 3.60 (s, 2H), 3.28 (t, J=6.8 Hz, 2H), 2.86-2.82 (m, 2H), 1.92-1.84 (m, 2H), 1.68-1.63 (m, 2H), 1.61-1.53 (m, 1H), 1.30-1.19 (m, 2H).

Example 13

Preparation of N-((1-(4-fluorobenzyl)piperidin-4-yl) methyl)-4-amino-5-chloro-2-methoxybenzamide Using 4-fluorobenzaldehyde and 4-amino-5-chloro-2-methoxy-(piperidin-4-ylmethyl)benzamide hydrochloride as starting materials, the title compound (215 mg) was obtained in the same manner as in <Example 9>.

$^1$H NMR (CDCl$_3$, 400 MHz): δ8.07 (s, 1H), 7.75-7.68 (m, 1H), 7.27-7.21 (m, 2H), 7.00-6.94 (m, 2H), 6.26 (s, 1H), 4.36 (s, 2H), 3.86 (s, 3H), 3.46-3.43 (m, 2H), 3.28 (t, J=6.4 Hz, 2H), 2.87-2.84 (m, 2H), 2.01-1.91 (m, 2H), 1.70-1.56 (m, 3H), 1.36-1.20 (m, 2H).

Example 14

Preparation of N-((1-(4-hydroxybenzyl)piperidin-4-yl) methyl)-4-amino-5-chloro-2-methoxybenzamide Using 4-hydroxybenzaldehyde and 4-amino-5-chloro-2-methoxy-(piperidin-4-ylmethyl)benzamide hydrochloride as starting materials, the title compound (75 mg) was obtained in the same manner as in <Example 9>.

$^1$H NMR (CDCl$_3$, 400 MHz): δ7.81 (s, 1H), 7.19 (d, J=8.8 Hz, 2H), 6.75 (s, J=8.8 Hz, 2H), 6.20 (s, 1H), 4.40 (s, 2H), 3.76 (s, 2H), 3.32-3.24 (m, 5H), 3.12-3.05 (m, 2H), 2.68-2.59 (m, 2H), 1.80-1.72 (m, 3H), 1.27-1.12 (m, 2H).

Example 15

Preparation of N-((1-(2-(indol-3-ylmethyl)piperidin-4-yl)methyl)-4-amino-5-chloro-2-methoxybenzamide Step 1: Preparation of 2-(indol-3-yl)ethanol Indole-3-acetic acid (5 g, 28.54 mmol) was dissolved in diethyl ether (100 mL) and the solution was cooled to 0° C. Lithium aluminum hydride (1.19 g, 31.39 mmol) was added thereto, followed by stirring for 4 hours. The reaction was terminated with the addition of water and a 10% sodium hydroxide solution. The reaction mixture was filtered through celite and concentrated under reduced pressure. The resulting residue was purified by column chromatography to afford the title compound (1.24 g, 27%).

$^1$H NMR (CDCl$_3$, 400 MHz): δ8.10-7.96 (bs, 1H), 7.61 (d, J=7.6 Hz, 1H), 7.36 (dd, J=8 Hz, 0.8 Hz, 1H), 7.24-7.17 (m, 1H), 7.15-7.07 (m, 2H), 3.92-3.87 (m, 2H), 3.05-3.00 (m, 2H).

Step 2: Preparation of 3-(2-bromoethyl)-indole (Compound of Formula 3)

2-(indol-3-yl)ethanol (623 mg, 3.86 mmol) was dissolved in dichloromethane (20 mL) and the solution was cooled to 0° C. Triphenylphosphine (1.12 g, 4.25 mmol) and tetra-bromomethane (1.41 g, 4.25 mmol) were then added thereto, followed by stirring for 1 hour. After the reaction was completed, the reaction mixture was concentrated under reduced pressure to remove the solvent. The resulting residue was purified by column chromatography to afford the title compound (765 mg, 88%).

$^1$H NMR (CDCl$_3$, 400 MHz): δ8.10-7.88 (bs, 1H), 7.58 (d, J=8 Hz, 1H), 7.38-7.34 (m, 1H), 7.24-7.20 (m, 1H), 7.19-7.08 (m, 2H), 3.65-3.60 (m, 2H), 3.35-3.30 (m, 2H).

Step 3: Preparation of N-((1-(2-(indol-3-yl)ethyl) piperidin-4-yl) methyl)-4-amino-5-chloro-2-methoxybenzamide Using 3-(2-bromoethyl)-indole and 4-amino-5-chloro-2-methoxy-(piperidin-4-ylmethyl)benzamide hydrochloride as starting materials, the title compound (190 mg) was obtained in the same manner as in <Example 1-3>.

$^1$H NMR (CDCl$_3$, 400 MHz): δ8.09 (s, 1H), 8.05 (s, 1H), 7.81-7.75 (m, 1H), 7.59 (d, J=7.6 Hz, 1H), 7.33 (d, J=8.4 Hz, 1H), 7.16 (t, J=7.2 Hz, 1H), 7.09 (t, J=7.6 Hz, 1H), 7.00 (d, J=1.6 Hz, 1H), 6.27 (s, 1H), 4.36 (s, 2H), 3.88 (s, 3H), 3,32 (t, J=6.4 Hz, 2H), 3.12-3.07 (m, 2H), 3.01-2.96 (m, 2H), 2.73-2.69 (m, 2H), 2.11-2.04 (m, 2H), 1.79-1.75 (m, 2H), 1.74-1.63 (m, 1H), 1.49-1.38 (m, 2H).

Example 16

Preparation of N-((1-(3-(tetrazol-1-yl)propyl)piperidin-4-yl)methyl)-4-amino-5-chloro-2-methoxybenzamide hydrochloride N-((1-(3-(tetrazol-1-yl)propyl)piperidin-4-yl)methyl)-4-amino-5-chloro-2-methoxybenzamide (Example 2) (517 mg, 1.27 mmol) was dissolved in ethanol (10 mL) and a 12N hydrochloride solution (0.16 mL, 1.90 mmol) was added thereto. The reaction mixture was stirred at room temperature for 12 hours and then filtered to afford the title compound (417 mg, 74%).

$^1$H NMR (DMSO-d6, 400 MHz): δ10.52 (s, 1H), 9.47 (s, 1H), 8.02-7.99 (m, 1H), 7.64 (s, 1H), 6.47 (s, 1H), 5.95 (s, 2H), 4.59-4.56 (m, 2H), 3.81 (s, 3H), 3.45-3.42 (m, 2H), 3.18-3.08 (m, 2H), 3.04-2.98 (m, 2H), 2.87-2.79 (m, 2H), 2.35-2.31 (m, 2H), 1.90-1.89 (m, 1H), 1.78-1.75 (m, 2H), 1.58-1.52 (m, 2H).

Example 17

Preparation of N-((1-(5-(1,2,3-triazol-1-yl)pentyl) piperidin-4-yl)methyl)-4-amino-5-chloro-2-methoxybenzamide hydrochloride Using N-((1-(5-(1,2,3-triazol-1-yl)pentyl)piperidin-4-yl)methyl)-4-amino-5-chloro-2-methoxybenzamide (Example 6) as a starting material, the title compound (112 mg, 35%) was obtained in the same manner as in <Example 16>.

$^1$H NMR (DMSO-d6, 400 MHz): δ10.06 (s, 1H), 8.14 (s, 1H), 8.02-7.99 (m, 1H), 7.71 (s, 1H), 7.64 (s, 1H), 6.47 (s, 1H), 5.95 (s, 2H), 4.40-4.37 (m, 2H), 3.81 (s, 3H), 3.40-3.32 (m, 2H), 3.18-3.12 (m, 2H), 2.96-2.90 (m, 2H), 2.84-2.75 (m, 2H), 1.87-1.70 (m, 7H), 1.59-1.48 (m, 2H), 1.25-1.17 (m, 2H).

Example 18

Preparation of N-((1-(3-(1,2,3-triazol-1-yl)propyl) piperidin-4-yl)methyl)-4-amino-5-chloro-2-methoxybenzamide hydrochloride Using N-((1-(3-(1,2,3-triazol-1-yl)propyl)piperidin-4-yl)methyl)-4-amino-5-chloro-2-methoxybenzamide (Example 7) as a starting material, the title compound (291 mg, 93%) was obtained in the same manner as in <Example 16>.

$^1$H NMR (DMSO-d6, 400 MHz): δ10.67 (s, 1H), 8.19 (s, 1H), 8.02-7.99 (m, 1H), 7.74 (s, 1H), 7.64 (s, 1H), 6.48 (s, 1H), 5.93 (bs, 2H), 4.51-4.47 (m, 2H), 3.81 (s, 3H), 3.44-3.41 (m, 2H), 3.34-3.31 (m, 2H), 2.98-2.96 (m, 2H), 2.87-2.79 (m, 2H), 2.34-2.29 9 m, 2H), 1.96-1.86 (m, 1H), 1.77-1.74 (m, 2H), 1.60-1.54 (m, 2H).

Example 19

Preparation of N-((1-((1-methylindol-3-yl)methyl) piperidin-4-yl)methyl)-4-amino-5-chloro-2-methoxybenzamide hydrochloride Using N-((1-((1-methylindol-3-yl)methyl)piperidin-4-yl) methyl)-4-amino-5-chloro-2-methoxybenzamide (Example 10) as a starting material, the title compound (237 mg, 44%) was obtained in the same manner as in <Example 16>.

$^1$H NMR (DMSO-d6, 400 MHz): δ10.34 (s, 1H), 7.96-7.93 (m, 1H), 7.79 (d, J=8 Hz, 1H), 7.64-7.59 (m, 2H), 7.47 (d, J=8 Hz, 1H), 7.22-7.19 (m, 1H), 7.14-7.10 (m, 1H), 6.47 (s, 1H), 4.36 (d, J=4.4 Hz, 2H), 3.81 (s, 3H), 3.79 (s, 3H), 3.40-3.37 (m, 2H), 3.14-3.11 (m, 2H), 2.90-2.82 (m, 2H), 1.77-1.71 (m, 3H), 1.53-1.48 (m, 2H).

Example 20

Preparation of N-((1-(4-fluorobenzyl)piperidin-4-yl) methyl)-4-amino-5-chloro-2-methoxybenzamide hydrochloride Using N-((1-(4-fluorobenzyl)piperidin-4-yl)methyl)-4-amino-5-chloro-2-methoxybenzamide (Example 13) as a starting material, the title compound (569 mg, 87%) was obtained in the same manner as in <Example 16>.

$^1$H NMR (DMSO-d6, 400 MHz): δ10.78 (s, 1H), 7.98-7.96 (m, 1H), 7.73-7.63 (m, 3H), 7.30-7.25 (m, 2H), 6.47 (s, 1H), 5.94 (s, 2H), 4.22 (d, J=4.8 Hz, 2H), 3.80 (s, 3H), 3.29-3.26 (m, 2H), 3.14-3.07 (m, 2H), 2.86-2.78 (m, 2H), 1.89-1.85 (m, 1H), 1.77-1.74 (m, 2H), 1.59-1.53 (m, 2H).

Example 21

Preparation of N-((1-(4-hydroxybenzyl)piperidin-4-yl) methyl)-4-amino-5-chloro-2-methoxybenzamide hydrochloride Using N-((1-(4-hydroxybenzyl)piperidin-4-yl)methyl)-4-amino-5-chloro-2-methoxybenzamide (Example 14) as a starting material, the title compound (158 mg, 97%) was obtained in the same manner as in <Example 16>.

$^1$H NMR (DMSO-d6, 400 MHz): δ10.25 (s, 1H), 7.98-7.96 (m, 1H), 7.63 (s, 1H), 7.34 (d, J=6.4 Hz, 2H), 6.80 (d, J=6.4 Hz, 2H), 6.47 (s, 1H), 4.08 (d, J=3.6 Hz, 2H), 3.80 (s, 3H), 3.28-3.25 (m, 2H), 3.15-3.12 (m, 2H), 2.82-2.74 (m, 2H), 1.77-1.62 (m, 3H), 1.54-1.48 (m, 2H).

Experimental Example 1

Binding Affinity of Compounds for 5-HT$_4$ Receptor

The binding affinity of the compounds for a human 5-HT$_4$ receptor was assayed according to the method as disclosed in the literature [Wyngaert et al., Journal of Neurochemistry, (1997) 69, 1810-1819]. For this purpose, COS-7 cells expressing the human 5-HT$_4$ receptor were constructed and homogenized to obtain membrane homogenates which were then used in binding assay experiments. For the binding assay, the membrane homogenates were respectively mixed and incubated with different concentrations of test materials and [H3]-GR113808 (Amersham Biosciences). The concentrations of the individual test materials were set to 4 μM, 1 μM, 0.25 μM, and 0.0625 μM, respectively, and the concentration of [H3]-GR113808 was set to 0.595 nM. After the incubation was completed, the reaction products were collected in GF/B glass fiber filters using a Packard cell harvester, and the bound radioactivity was then determined using a liquid cell scintillation counter (Packard TopCount NXT™, Perkin Elmer). Specific binding of the radioligand to the 5-$HT_4$ receptor was calculated by subtracting the non-specific binding of the radioligand from the total radioligand binding. $IC_{50}$ was calculated from % inhibition of specific binding of the radioligand to the 5-$HT_4$ receptor, with respect to varying concentrations of the test materials. The results are given in Table 1 below.

TABLE 1

| Compounds | $IC_{50}$ (nM) |
|---|---|
| Cisapride | 0.362 |
| Example 1 | 0.226 |
| Example 2 | 0.164 |
| Example 3 | 0.039 |
| Example 4 | 0.229 |
| Example 5 | 0.005 |
| Example 6 | 0.103 |
| Example 7 | 0.067 |
| Example 8 | 0.182 |
| Example 9 | 0.267 |
| Example 10 | 0.076 |
| Example 11 | 0.454 |
| Example 12 | 0.421 |
| Example 13 | 0.134 |
| Example 14 | 0.375 |
| Example 15 | 0.002 |

As can be seen from Table 1, the compounds of the present invention inhibited specific binding of the radioligand to the 5-$HT_4$ receptor at a concentration similar to or lower than that of cisapride as a control, thus representing that the inventive compounds have a strong binding affinity for 5-$HT_4$ receptor.

Experimental Example 2

Evaluation of Gastric Emptying

Evaluation of gastric emptying was carried out based on the method described in Iwanaga Y, et al., *Jpn J Pharmacol.* 1991, 56(3), 261-269. As experimental animals, SD rats (240 to 250 g) were used and divided into groups (n=5 to 6). On the day prior to the experiment, animals were fasted for 18 hours. Test materials were formulated as suspensions thereof in 0.5% (w/v) methylcellulose and were orally administered to the animals at a dose of 5 mg/kg. 1 hour after the oral administration of the test materials, 2 mL of a semi-solid diet was orally administered to the animals. The semi-solid diet was in the form of porridge formulated by pulverizing a standard solid diet together with distilled water in a mixer. 50 minutes after the administration of the semi-solid diet, the animals were sacrificed by cervical dislocation. After carrying out an abdominal incision, the stomach was extracted from the animals. The weight of diet remaining in the stomach was measured to thereby determine the gastric emptying rate (%). The gastric emptying rate was calculated according to the following equation. The results are given in Table 2 below.

Gastric Emptying Rate (%)=(1−X/Y)*100

X: Weight of diet remaining in the stomach extracted 50 minutes after administration of meal Y: Weight of diet remaining in the stomach extracted immediately after administration of meal

TABLE 2

| Compounds | Gastric emptying rate (%) |
|---|---|
| Control (0.5% methylcellulose) | 32.2 |
| Example 1 | 43.0 |
| Example 2 | 52.8 |
| Example 3 | 45.2 |
| Example 4 | 46.4 |
| Example 5 | 52.0 |
| Example 6 | 46.0 |
| Example 7 | 56.1 |
| Example 8 | 49.1 |
| Example 9 | 51.2 |
| Example 10 | 59.1 |
| Example 11 | 43.1 |
| Example 12 | 62.0 |
| Example 13 | 52.3 |
| Example 14 | 42.1 |
| Example 15 | 41.3 |

As can be seen from Table 2, the administration of the compounds of the present invention resulted in a remarkable improvement of gastric emptying, as compared to the methylcellulose-treated group as a control, thus representing that the inventive compounds promote gastrointestinal motility.

Experimental Example 3

Acute Oral Toxicity of Compounds in Mice

In order to examine acute toxicity of the compounds in accordance with the present invention, the following experiment was carried out.

200 mg of each of Example compounds was triturated in 1% hydroxypropyl methyl-cellulose, and the resulting triturations were then orally administered to 5-week old male ICR mice (20 g±2 g, n=5) at a dose of 1 g/10 mL/kg. The minimum lethal dose (MLD, mg/kg) of the individual compounds was investigated by the observation of the mortality, body weight, clinical symptoms and the like of animals over the entire experimental period of 2 weeks. The results are given in Table 3 below.

TABLE 3

| Compounds | Minimum lethal dose (MLD, mg/kg) |
|---|---|
| Example 1 | >1000 |
| Example 2 | >1000 |
| Example 3 | >1000 |
| Example 4 | >1000 |
| Example 5 | >1000 |
| Example 6 | >1000 |
| Example 7 | >1000 |
| Example 8 | >1000 |
| Example 9 | >1000 |
| Example 10 | >1000 |
| Example 11 | >1000 |
| Example 12 | >1000 |
| Example 13 | >1000 |
| Example 14 | >1000 |
| Example 15 | >1000 |

As can be seen from the acute toxicity test results of Table 3, all of the compounds used in the test exhibited an MLD of more than 1000 mg/kg, thus representing that the inventive compounds are safe for use.

Experimental Example 4

Binding Affinity of Drug Compounds for hERG Receptor

The binding affinity of the compounds for the human ether-a-go-go-related gene (hERG) potassium (K+) channel which is associated with cardiac QT prolongation was assayed in MDS Pharma Service (Catalog No. 265900). Membrane homogenates were obtained from mammalian HEK-293 cells expressing the hERG potassium channel and then used in the binding assay experiment. For the binding assay experiment, the membrane homogenates were respectively mixed and incubated with 10 μM of test materials and 1.5 nM of [H3]-Astemizole (Perkin Elmer). After the incubation was completed, the radioactivity bound to the hERG K+ channel was counted. The affinity of each test material for the hERG K+ channel was calculated from % inhibition of specific binding of the radioligand to the hERG K+ channel, resulting from the action of the test material. The results are given in Table 4 below.

TABLE 4

| Compounds | Inhibition (% at 10 μM) |
|---|---|
| Example 1 | 1 |
| Example 2 | 4 |
| Example 4 | 14 |
| Example 6 | 8 |
| Example 7 | 7 |
| Example 8 | 15 |
| Example 9 | 6 |
| Example 11 | 21 |
| Example 12 | 32 |
| Example 13 | 52 |
| Example 14 | 40 |

Incidence of cardiac arrhythmia which is a fatal adverse effect is due to the cardiac QT prolongation that results from an excessively high affinity of the drug for the hERG receptor. The compounds of the present invention exhibited an inhibition rate of less than 50% even at a dose of 10 μM and therefore have a low binding affinity for the hERG receptor, thus suggesting that the inventive compounds exhibit a significantly low risk of causing arrhythmia.

The invention claimed is:

1. A compound of Formula 1:

[Formula 1]

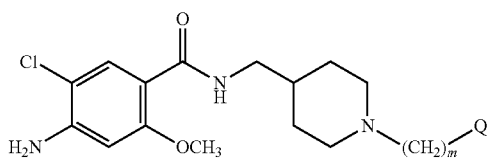

or a pharmaceutically acceptable salt thereof, wherein:
m is an integer of 1 to 10; and
Q is either:
(i) a heteroaromatic ring that is selected from the group consisting of triazole, tetrazole, indole, imidazole and pyrrole and substituted by 0, 1, 2, or 3 substituents selected from among alkyl, alkoxy, hydroxy, cyano, nitro and halogen; or
(ii) a phenyl substituted by 1, 2, or 3 substituents selected from among alkyl, hydroxy, cyano, nitro and fluoro.

2. The compound of claim 1, wherein:
m is an integer of 1 to 5; and
Q is either:
(i) a heteroaromatic ring that is selected from the group consisting of triazole, tetrazole, indole, imidazole and pyrrole and substituted by 0, 1, 2 or 3 substituents selected from among $C_1$-$C_4$ alkyl, $C_1$-$C_4$ alkoxy, hydroxy and halogen; or
(ii) a phenyl substituted by 1, 2 or 3 substituents selected from among $C_1$-$C_4$ alkyl, hydroxy and fluoro.

3. A compound selected from among the following compounds:

N-((1-(3-(1,2,4-triazol-1-yl)propyl)piperidin-4-yl)methyl)-4-amino-5-chloro-2-methoxybenzamide, N-((1-(3-(tetrazol-1-yl)propyl)piperidin-4-yl)methyl)-4-amino-5-chloro-2-methoxybenzamide, N-((1-(3-(indol-1-yl)propyl)piperidin-4-yl)methyl)-4-amino-5-chloro-2-methoxybenzamide, N-((1-(3-(2-methylimidazol-1-yl)propyl)piperidin-4-yl)methyl)-4-amino-5-chloro-2-methoxybenzamide, N-((1-(5-(indol-1-yl)pentyl)piperidin-4-yl)methyl)-4-amino-5-chloro-2-methoxybenzamide, N-((1-(5-(1,2,3-triazol-1-yl)pentyl)piperidin-4-yl)methyl)-4-amino-5-chloro-2-methoxybenzamide, N-((1-(3-(1,2,3-triazol-1-yl)propyl)piperidin-4-yl)methyl)-4-amino-5-chloro-2-methoxybenzamide, N-((1-(3-(1,2,3-triazol-2-yl)propyl)piperidin-4-yl)methyl)-4-amino-5-chloro-2-methoxybenzamide, N-((1-((1-methylindol-3-yl)methyl)piperidin-4-yl)methyl)-4-amino-5-chloro-2-methoxybenzamide, N-((1-(imidazol-2-ylmethyl)piperidin-4-yl)methyl)-4-amino-5-chloro-2-methoxybenzamide, N-((1-((1-methylpyrrol-2-yl)methyl)piperidin-4-yl)methyl)-4-amino-5-chloro-2-methoxybenzamide, N-((1-(4-fluorobenzyl)piperidin-4-yl)methyl)-4-amino-5-chloro-2-methoxybenzamide, N-((1-(4-hydroxybenzyl)piperidin-4-yl)methyl)-4-amino-5-chloro-2-methoxybenzamide, N-((1-(2-(indol-3-yl)ethyl)piperidin-4-yl)methyl)-4-amino-5-chloro-2-methoxybenzamide, N-((1-(3-(tetrazol-1-yl)propyl)piperidin-4-yl)methyl)-4-amino-5-chloro-2-methoxybenzamide hydrochloride, N-((1-(5-(1,2,3-triazol-1-yl)pentyl)piperidin-4-yl)methyl)-4-amino-5-chloro-2-methoxybenzamide hydrochloride, N-((1-(3-(1,2,3-triazol-1-yl)propyl)piperidin-4-yl)methyl)-4-amino-5-chloro-2-methoxybenzamide hydrochloride, N-((1-((1-methylindol-3-yl)methyl)piperidin-4-yl)methyl)-4-amino-5-chloro-2-methoxybenzamide hydrochloride, N-((1-(4-fluorobenzyl)piperidin-4-yl)methyl)-4-amino-5-chloro-2-methoxybenzamide hydrochloride, N-((1-(4-hydroxybenzyl)piperidin-4-yl)methyl)-4-amino-5-chloro-2-methoxybenzamide hydrochloride, and a pharmaceutically acceptable salt thereof.

4. A method for preparing a compound of Formula 1 of claim 1, comprising:

reacting a compound of Formula 2:

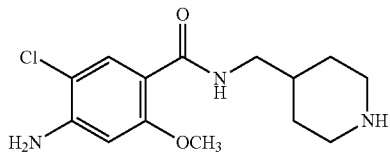

[Formula 2]

or a pharmaceutically acceptable salt thereof with a compound of Formula 3:

 [Formula 3]

wherein:

Y is a halogen atom or $C_1$-$C_4$ alkylsulfonate;

m is an integer of 1 to 10; and

Q is either:
(i) a heteroaromatic ring substituted by 0, 1, 2, or 3 substituents selected from among alkyl, alkoxy, hydroxy, cyano, nitro and halogen; or
(ii) a phenyl substituted by 1, 2, or 3 substituents selected from among alkyl, hydroxy, cyano, nitro and fluoro;

in the presence of a base to introduce the compound of Formula 3 at an amine of the 1-position of the piperidine ring of the compound of Formula 2 or the pharmaceutically acceptable salt thereof, thereby preparing the compound of Formula 1.

5. The method of claim 4, wherein the base is selected from among potassium carbonate, potassium iodide, triethylamine, diisopropylethylamine and mixtures thereof.

6. A method for preparing a compound of Formula 1:

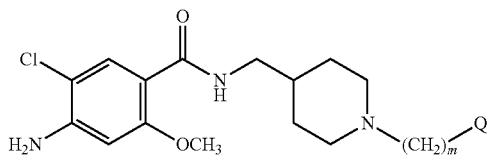

[Formula 1]

wherein m is 1, or a pharmaceutically acceptable salt thereof, comprising:

reacting a compound of formula 2:

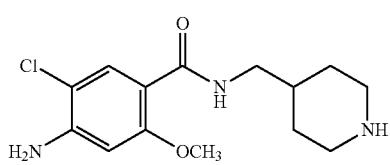

[Formula 2]

or a pharmaceutically acceptable salt thereof with a compound of formula 11:

[Formula 11]

wherein:

Q is either:
(i) a heteroaromatic ring substituted by 0, 1, 2, or 3 substituents selected from among alkyl, alkoxy, hydroxy, cyano, nitro and halogen; or
(ii) a phenyl substituted by 1, 2, or 3 substituents selected from among alkyl, alkoxy, hydroxy, cyano, nitro and fluoro;

in the presence of a reducing agent to prepare the compound of Formula 1.

7. The method of claim 6, wherein the reducing agent is sodium cyanoborohydride and acetic acid, or sodium borohydride.

8. The method of claim 4, wherein the compound of Formula 2 or the pharmaceutically acceptable salt thereof is prepared by:

(1) reacting a compound of Formula 4:

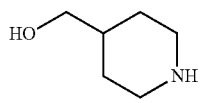

[Formula 4]

with an amine protecting group-introducing reagent to introduce an amine protecting group at an amine of the 1-position of the piperidine ring of the compound of Formula 4, thereby obtaining a compound of Formula 5:

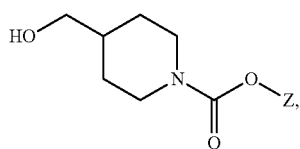

[Formula 5]

wherein Z is $C_1$-$C_4$ alkyl;

(2) reacting the hydroxy of the compound of Formula 5 with N-bromosuccinimide and carbon tetrabromide, or with $C_1$-$C_4$ alkyl sulfonyl halide in the presence of a base to obtain a compound of Formula 6:

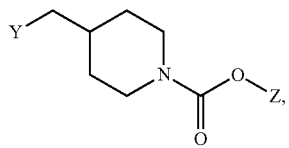

[Formula 6]

wherein Y is a halogen atom or $C_1$-$C_4$ alkylsulfonate;

(3) reacting the substituent Y of the compound of Formula 6 with sodium azide to obtain a compound of Formula 7:

[Formula 7]

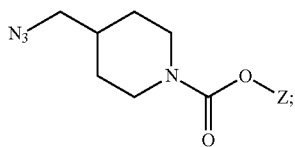

(4) reducing the azido substituent of the compound of Formula 7 into an amine in the presence of a reducing agent to obtain a compound of Formula 8:

[Formula 8]

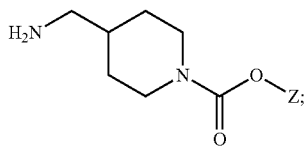

(5) reacting the compound of Formula 8 with a compound of Formula 9:

[Formula 9]

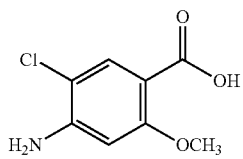

in the presence of an amide bond formation-inducing reagent to obtain a compound of Formula 10:

[Formula 10]

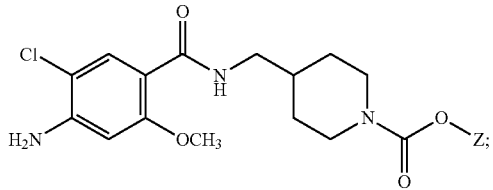

and (6) deprotecting the amine protecting group of the piperidine ring of the compound of Formula 10 in the presence of a base or acid.

9. The method of claim 8, wherein the amine protecting group-introducing reagent of Step (1) is di-t-butyl dicarbonate or ethyl chloroformate in the presence of a tertiary amine base.

10. The method of claim 8, wherein the $C_1$-$C_4$ alkyl sulfonyl halide of Step (2) is methane sulfonyl chloride, methane sulfonyl bromide or methane sulfonyl fluoride.

11. The method of claim 8, wherein the reducing agent of Step (4) is triphenylphosphine or lithium aluminum hydride.

12. The method of claim 8, wherein the amide bond formation-inducing reagent of Step (5) is N-(3-dimethyl-aminopropyl)-N'-ethylcarbodiimide hydrochloride and 1-hydroxybenzotriazole in the presence of a base, ethyl chloroformate in the presence of a base, or carbodiimidazole in the absence of a base.

13. The method of claim 8, wherein the base or acid of Step (6) is selected from among hydrochloric acid, trifluoroacetic acid and potassium hydroxide.

14. A 5-HT4 receptor agonist, comprising a compound of Formula of claim 1:

[Formula 1]

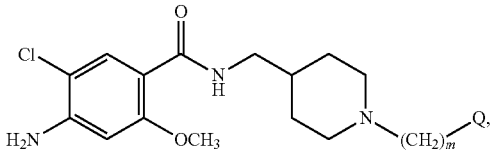

or a pharmaceutically acceptable salt thereof,
wherein:
m is an integer of 1 to 10; and
Q is either:
(i) a heteroaromatic ring that is selected from the group consisting of triazole, tetrazole, indole, imidazole and pyrrole and substituted by 0, 1, 2, or 3 substituents selected from among alkyl, alkoxy, hydroxy, cyano, nitro and halogen; or a pharmaceutically acceptable salt thereof; or
(ii) a phenyl substituted by 1, 2, or 3 substituents selected from among alkyl, hydroxy, cyano, nitro and fluoro.

15. The agonist of claim 14, wherein:
m is an integer of 1 to 5; and
Q is either:
(i) a heteroaromatic ring that is selected from the group consisting of triazole, tetrazole, indole, imidazole and pyrrole and substituted by 0, 1, 2, or 3 substituents selected from among $C_1$-$C_4$ alkyl, $C_1$-$C_4$ alkoxy, hydroxy and halogen; or
(ii) a phenyl substituted by 1, 2 or 3 substituents selected from among $C_1$-$C_4$ alkyl, hydroxy and fluoro.

16. A 5-HT4 receptor agonist, comprising a compound selected from among the following compounds:
N-((1-(3-(1,2,4-triazol-1-yl)propyl)piperidin-4-yl)methyl)-4-amino-5-chloro-2-methoxybenzamide,
N-((1-(3-(tetrazol-1-yl)propyl)piperidin-4-yl)methyl)-4-amino-5-chloro-2-methoxybenzamide,
N-((1-(3-(indol-1-yl)propyl)piperidin-4-yl)methyl)-4-amino-5-chloro-2-methoxybenzamide,
N-((1-(3-(2-methylimidazol-1-yl)propyl)piperidin-4-yl)methyl)-4-amino-5-chloro-2-methoxybenzamide,
N-((1-(5-(indol-1-yl)pentyl)piperidin-4-yl)methyl)-4-amino-5-chloro-2-methoxybenzamide,
N-((1-(5-(1,2,3-triazol-1-yl)pentyl)piperidin-4-yl)methyl)-4-amino-5-chloro-2-methoxybenzamide,
N-((1-(3-(1,2,3-triazol-1-yl)propyl)piperidin-4-yl)methyl)-4-amino-5-chloro-2-methoxybenzamide,
N-((1-(3-(1,2,3-triazol-2-yl)propyl)piperidin-4-yl)methyl)-4-amino-5-chloro-2-methoxybenzamide,
N-((1((1-methylindol-3-yl)methyl)piperidin-4-yl)methyl)-4-amino-5-chloro-2-methoxybenzamide,
N-((1-(imidazol-2-ylmethyl)piperidin-4-yl)methyl)-4-amino-5-chloro-2-methoxybenzamide,
N-((1-((1-methylpyrrol-2-yl)methyl)piperidin-4-yl)methyl)-4-amino-5-chloro-2-methoxybenzamide,
N-((1-(4-fluorobenzyl)piperidin-4-yl)methyl)-4-amino-5-chloro-2-methoxybenzamide, N-((1-(4-hydroxybenzyl)piperidin-4-yl)methyl)-4-amino-5-chloro-2-methoxybenzamide, N-((1-(2-(indol-3-yl)ethyl)piperidin-4-yl)methyl)-4-amino-5-chloro-2-methoxybenzamide, N-((1-(3-(tetrazol-1-yl)propyl)piperidin-4-yl)methyl)-4-amino-5-chloro-2-methoxybenzamide hydrochloride, N-((1-(5-(1,2,3-triazol-1-yl)pentyl)piperidin-4-yl)methyl)-4-amino-5-chloro-2-methoxybenzamide hydrochloride, N-((1-(3-(1,2,3-triazol-1-yl)propyl)piperidin-4-yl)methyl)-4-amino-5-chloro-2-methoxybenzamide hydrochloride, N-((1((1-methylindol-3-yl)methyl)piperidin-4-yl)methyl)-4-amino-5-chloro-2-methoxybenzamide hydrochloride, N-((1-(4-fluorobenzyl)piperidin-4-yl)methyl)-4-amino-5-chloro-2-methoxybenzamide hydrochloride, N-((1-(4-hydroxybenzyl)piperidin-4-yl)methyl)-4-amino-5-chloro-2-methoxybenzamide hydrochloride, and a pharmaceutically acceptable salt thereof.

17. A composition, comprising the agonist of any one of claims 14 to 16.

18. A method for the treatment or alleviation of a disease due to attenuated efficacy of a 5-HT4 receptor, comprising administering a 5-HT4 receptor agonist containing a compound of Formula 1 of any one of claims 1 to 3 or a pharmaceutically acceptable salt thereof as an active ingredient to a mammal in need of 5-HT4 receptor agonistic effects, wherein the disease is selected from among gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, emesis, migraine, cardiovascular disorder, cardiac failure, cardiac arrhythmia, and apnea syndrome.

19. The compound of claim 1, wherein Q is a heteroaromatic ring that is selected from among triazole, tetrazole, indole, imidazole and pyrrole.

20. The agonist of claim 14, wherein Q is a heteroaromatic ring that is selected from among triazole, tetrazole, indole, imidazole and pyrrole.

21. The method of claim 18, wherein the mammal is a human.

* * * * *

UNITED STATES PATENT AND TRADEMARK OFFICE
CERTIFICATE OF CORRECTION

PATENT NO. : 9,221,790 B2
APPLICATION NO. : 13/641867
DATED : December 29, 2015
INVENTOR(S) : Kim et al.

It is certified that error appears in the above-identified patent and that said Letters Patent is hereby corrected as shown below:

IN THE CLAIMS:

Column 26, line 7 to line 31, should read,

14. A 5-HT4 receptor agonist, comprising a compound of Formula 1 of claim 1:

[Formula 1]

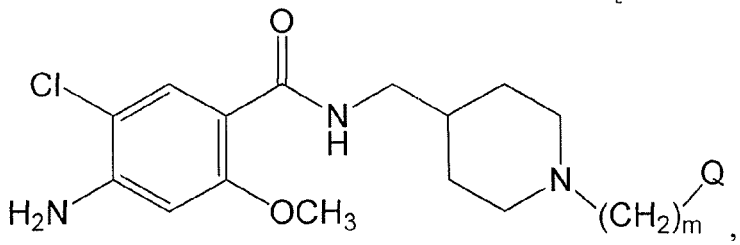

or a pharmaceutically acceptable salt thereof,
wherein:
  m is an integer of 1 to 10; and
  Q is either:
    (i) a heteroaromatic ring that is selected from the group consisting of triazole, tetrazole, indole, imidazole and pyrrole and substituted by 0, 1, 2, or 3 substituents selected from among alkyl, alkoxy, hydroxy, cyano, nitro and halogen; or a pharmaceutically acceptable salt thereof; or
    (ii) a phenyl substituted by 1, 2, or 3 substituents selected from among alkyl, hydroxy, cyano, nitro and fluoro.

Signed and Sealed this
Twenty-third Day of August, 2016

Michelle K. Lee
*Director of the United States Patent and Trademark Office*